(12) United States Patent
Rogozinski

(10) Patent No.: US 6,379,354 B1
(45) Date of Patent: *Apr. 30, 2002

(54) SPINAL IMPLANT AND METHOD

(76) Inventor: Chaim Rogozinski, 3223 Front Rd., Jacksonville, FL (US) 32217

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,838

(22) Filed: Nov. 3, 1997

Related U.S. Application Data

(63) Continuation-in-part of application No. 08/898,862, filed on Jul. 23, 1997, now Pat. No. 5,904,682, which is a division of application No. 08/692,821, filed on Jul. 29, 1996, now Pat. No. 5,716,357, which is a continuation-in-part of application No. PCT/US94/05815, filed on May 25, 1994, which is a continuation-in-part of application No. 08/131,947, filed on Oct. 8, 1993, now abandoned.

(51) Int. Cl.7 .............................................. A61B 17/70
(52) U.S. Cl. ............................... 606/61; 606/69; 606/72
(58) Field of Search ............................. 606/61, 69, 70, 606/71, 72, 73, 75, 104, 105; 623/17.11

(56) References Cited

U.S. PATENT DOCUMENTS

| | | | | |
|---|---|---|---|---|
| 3,693,616 A | * | 9/1972 | Roaf et al. ..................... | 606/61 |
| 4,085,744 A | * | 4/1978 | Lewis et al. ................... | 606/61 |
| 4,959,065 A | * | 9/1990 | Arnett et al. .................. | 606/69 |
| 5,092,893 A | * | 3/1992 | Smith ........................... | 606/60 |
| 5,147,361 A | * | 9/1992 | Ojima et al. .................... | 606/61 |
| 5,234,431 A | * | 8/1993 | Keller .......................... | 606/61 |
| 5,415,661 A | * | 5/1995 | Holmes ........................ | 606/69 |

* cited by examiner

Primary Examiner—David O. Reip
Assistant Examiner—Julian W. Woo
(74) Attorney, Agent, or Firm—Thomas C. Saitta

(57) ABSTRACT

An apparatus, method and system for treating spinal conditions by moving or spatially fixing at least one vertebra relative to another vertebra. The invention includes a link member the ends of which are configured to be secured to adjacent vertebrae and which are offset from a central portion of the link member. The link members can be in the form of a C-shaped or V-shaped rod or plate to form the offset. The offset provides increased bone volume that can be used for grafts or fusion. Attachment structure in the form of bone screws, bolts, or hook members are provided to secure the link members to respective vertebrae or other bones. A plurality of link members can be connected in chain-like fashion to connect multiple points on a plurality of vertebrae or other bones even though those points are nonlinear. In another aspect of the invention, a multi-directional attachment member is provided and may be used with the link members to form a spinal implant or external bone fixation system.

27 Claims, 10 Drawing Sheets

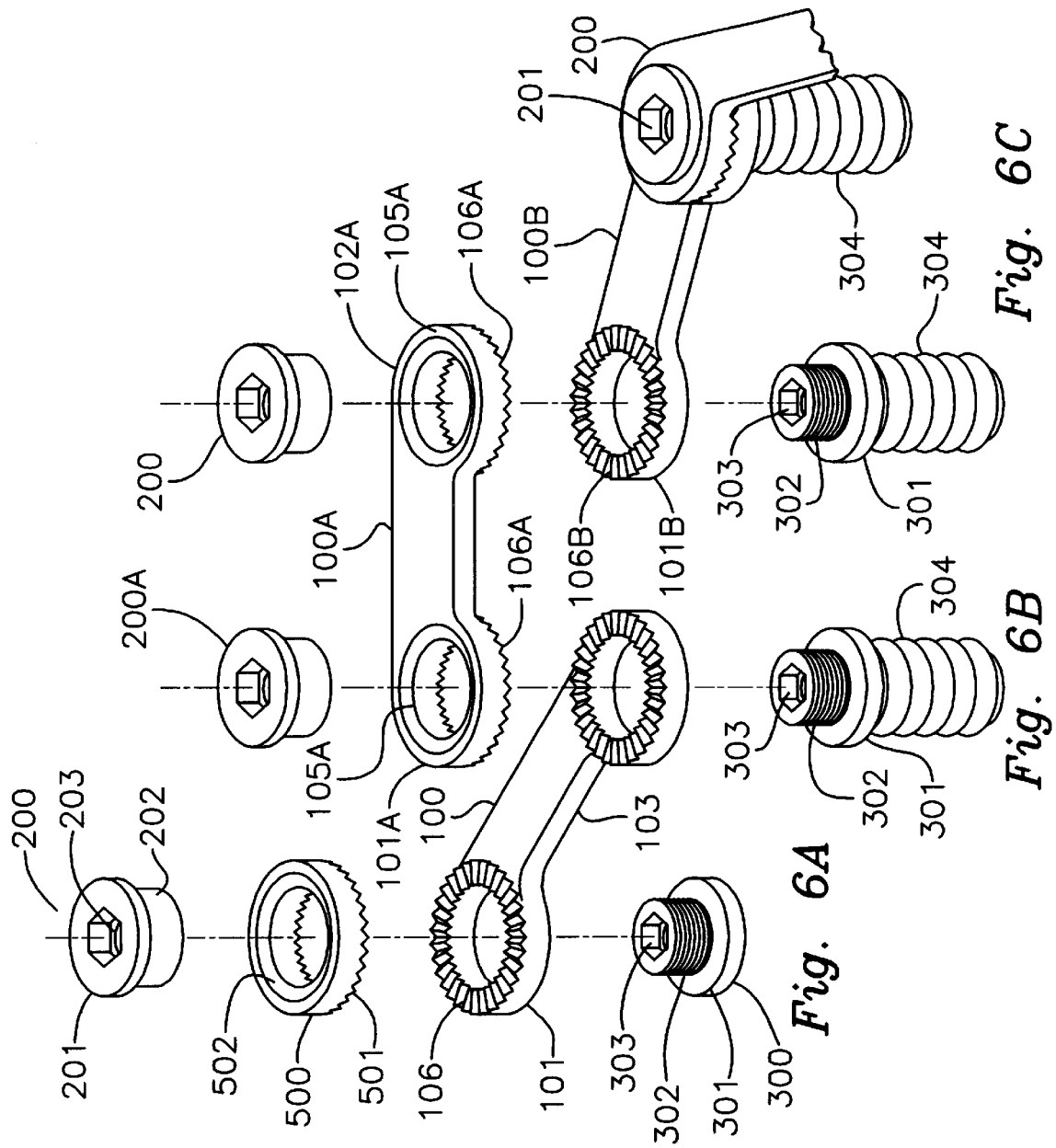

SPINAL IMPLANT AND METHOD

This application is a continuation-in-part of application Ser. No. 08/898,862 filed Jul. 23, 1997, now U.S. Pat. No. 5,904,682 which is a division of application Ser. No. 03/692,821 filed Jul. 29, 1996, now U.S. Pat. No. 5,716,357 which is a continuation-in-part of PCT/US94/05815 filed May 25, 1994 which is a continuation-in-part of Ser. No. 08/131,947 filed Oct. 8, 1993, now abandoned.

FIELD OF THE INVENTION

The present invention relates generally to apparatus and methods for spinal abnormalities.

DESCRIPTION OF THE RELEVANT ART

The prior art includes many different apparatus and methods for treating spinal conditions. Known apparatus may utilize elongate plate members having several aligned collinear openings for screws fixed in vertebrae which frequently are not collinear. To match the collinear screw openings with non-collinear fixed screws, the physician must attempt to contour the plate in the frontal plane. See FIGS. A and B which illustrate the traditional rod or plate system.

Alternatively, the screws may be bent to accommodate the plate openings. Both alternatives may be intraoperatively impossible or impractical.

Placement in a less than optimum position or trajectory in the pedicle to provide alignment with the plate openings may require undesirable pedicle cutout or fracture and nerve root injury.

Other known apparatus for treating spinal deformities are disclosed in U.S. Patent Nos. 5,104,412 and 5,181,917. These apparatus comprise elongate rod members combined with vertebra engaging means. The rods are essentially straight with the consequent need for specially formed connectors.

Accordingly, there is a need in the art for a method and apparatus for treating spinal conditions which avoids the problems of the prior art, permits attachment to nonlinear points on adjacent vertebrae, and provides increased bone volume for grafts or fusion.

SUMMARY OF THE INVENTION

The present invention provides an apparatus and method or system for treating spinal conditions by moving a vertebra to a desired position with respect to additional vertebrae or maintaining the vertebra in the desired position.

The apparatus of the present invention may include a plurality of link members that can be secured to adjacent vertebrae in chain-like fashion utilizing pedicle bolts or screws that are not collinear with each other. Use of the link members permits subdivision of multiple nonlinear pedicle fixation points into two point units interconnectable with a single link member.

The present invention thus facilitates multiple point fixation, schematically shown by FIG. B, using two points at a time to overcome the problem in the prior art of nonalignment between plate openings and pedicle screws. The links, once secured to the pedicle screw or bolt with a locking nut, form a chain. The result is a construct securely affixed to the vertebrae.

The link members are in the form of plates or rods with opposite end portions and a central portion. The links may be generally flat precontoured, for example, to correct lordosis or kyphosis or to impart torsion. Alternatively, the flat links may be contoured by surgeon incident an operative procedure. The opposite end portions each have an aperture therein configured to receive attachment means affixed to the pedicle of adjacent vertebrae. The central portion for each link member is preferably offset from the end portions to expose substantial portions of adjacent vertebrae to which the link member may be attached. The invention also includes links in which the central portion is not offset.

This offset provides increased vertebrae bone volume, useful bone grafts and fusion as compared with prior art apparatus which overlie the vertebra surface. In addition, the present invention permits visualization of bony maturation using plain X-rays since the links do not overlie the graft area.

The links may be used with pedicle screws, bolts, or pedicle or laminar hooks. A combination of hooks and screws or bolts can be used as well depending on the particular application of the invention. For example, a laminar hook can be used on a lamina that is being fused to avoid damaging its associated facet (joint) such as would be caused by a screw or bolt.

The surface of the link member of the present invention is preferably provided with radial cuts or other means adjacent the apertures in the end portions for enhancing the locking engagement of the links with a pedicle bolt, screw, hook, another link or other spinal implant members. The bolt or hook has a threaded extension portion that cooperates with a locking nut, and a wedge-shaped washer if needed, to secure an end of the link member to a vertebra.

The wedge-shaped washer compensates for a lack of parallelism in the axial plane between adjacent bolts or screws.

An additional aspect of the present invention is that link members may be used to secure contralateral chains (formed as described above) to each other at their ends, and/or points intermediate their ends, to form a quadrilateral or ladder-shaped construct having increased torsional stability.

It is frequently difficult to make a tight connection between a non-aligned series of implanted bone bolts. For example, in a spinal construct, bone bolts are rarely aligned for connection of a plate or rod. The adjacent bone screws are usually independently located with respect to each other in three dimensional space, which creates an offset distance of some kind between the bolt and the plate/rod connection. See FIG. A. The offset problem has been addressed by providing connectors that accommodate the non-linearity of the adjacent bolts implanted in a series. There is a limit to the adjustability of the currently available connectors when S used with traditional bone bolts and bone screws.

An important object of the invention is to provide polydirectional bone bolts or screws with effective pedicle purchase which may rotate up to 360° for sagittal plane variability. Sagittal plane adjustment is achieved through the rotation of the polydirectional screw head reducing the need for significant contouring of the associated links. See generally FIGS. A and B (comparing traditional rod and plate system with the link and polydirectional screw system of this invention).

A multi-angle bone bolt is also needed for use in any bone fixation system in which uneven bone portions are to be connected to a bolt whereas angulation of upper and lower portions of the bolt will provide a more effective and secure bone fixation system.

FIGS. 9A, 9B, 9C, 9D, 10A and 10B of application Ser. No. 08/692,821, now U.S. Pat. No. 5,716,357 which is a continuation of Ser. No. 08/448,566 (PCT/US94/11463) illustrate spinal fixation devices including one form of a multi-angle or multi-directional screw.

The invention permits manipulation of the spine before the link is placed with consequently more accurate, quantifiable adjustments and improved visualization. The link design allows medialized placement in the lumbar spine and lateralized placement in the thoracic spine. Greater surgeon accessibility to the bone graft site optimizes the graft bed and the useful volume of bone graft.

BRIEF DESCRIPTION OF THE DRAWINGS

FIG. 1A is a perspective view of one form of a multi-directional attachment device constructed according to the present invention.

FIG. 1B is a perspective view of a multi-directional attachment device depicted in FIG. 1A showing a modification thereto.

FIG. 1C is a perspective exploded view of the multi-directional attachment device depicted in FIG. 1A. FIG. 1D is a perspective view of a multi-directional attachment device according to another embodiment of the present invention.

FIG. 2A is a front elevational view of the link member and multi-directional attachment device of the present invention used as an external bone fixation apparatus.

FIG. 2B is a side elevational view of the link member and multi-directional attachment device of the present invention used as an external bone fixation apparatus in a two plane fixation system.

FIG. 3 is a front elevational view of the link member and multi-directional attachment device of the present invention used as a pelvic bone fixation apparatus.

FIGS. 6A–6C are exploded views showing one mode of assembling implant members of the invention including a bone screw, a plurality of links, a link tie means and end caps of the invention.

DETAILED DESCRIPTION OF THE FIGURES

Figure 1A:
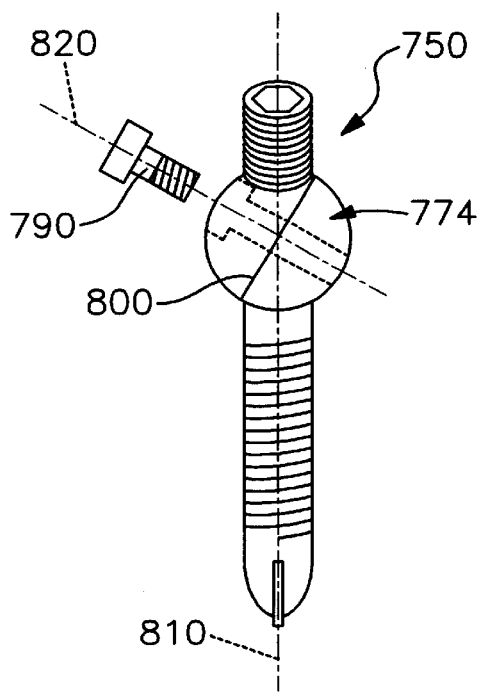
FIGS. 1A, 1B, 1C and 1D are identical to FIGS. 9A–9D in application Ser. No. 08/692,821. As stated in that application.
Figure 1B:
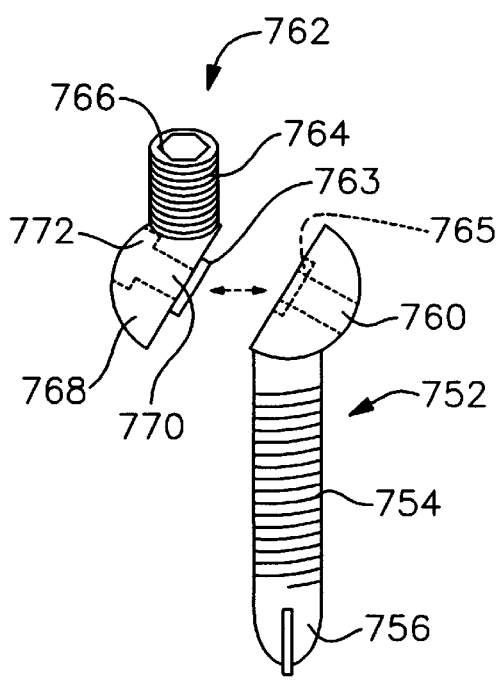
Figure 1C:
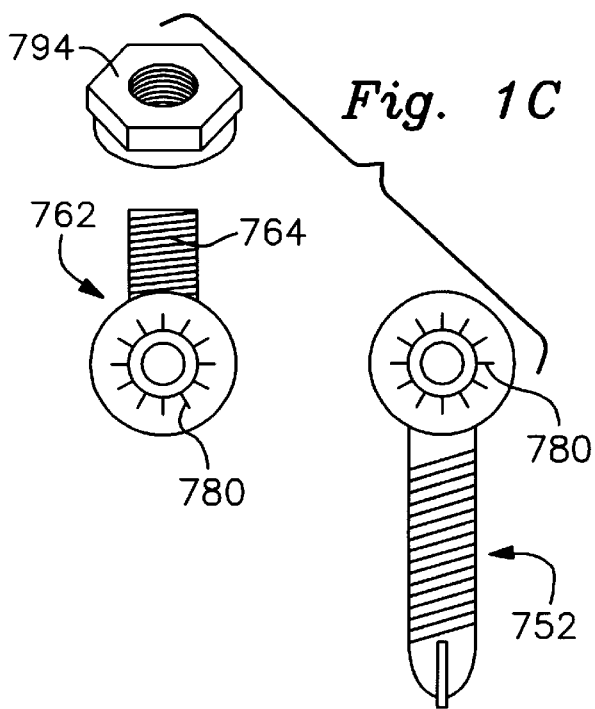

Referring now to FIGS. 1A–1C, a multi-directional attachment device constructed according to one aspect of the invention is indicated generally by reference numeral 750. The multi-directional attachment device 750 may be used with the above-described spinal treatment apparatus, e.g., in place of or in addition to any fixed bone bolt, e.g., the bolt 600 shown by FIG. 7 or with various other spinal treatment apparatus or, still further, device 750 may be used with fixation apparatus for treating other bones than those in the spine. For example, the element 750 may be used with external fixation apparatus for treating long bones and the pelvis.

Multi-directional attachment device 750 includes two portions, namely, screw portion 752 and bolt portion 754. Screw portion 752 has an elongated section extending between opposite ends 756, 758, which elongated section has helical threads 754 (or another suitable cutting surface) formed thereon for engaging a bore formed in a vertebra or other bone (not shown). The screw portion 752 preferably has a hemispherically-shaped end 758 with a bore 760 extending therethrough. The end 758 of screw portion 752 has a flat face (FIG. 1C) with serrations or other interdigitating structure 780 formed thereon for reasons described below. The bore 760 preferably is centrally located with respect to hemispherically-shaped end 758 as seen in FIGS. 1B and 1C.

Bolt portion 762 includes opposite end portions 766 and 768. A threaded portion 764 extends from end 766 and includes threads (or other means) for engaging a locking nut after an apertured (or slotted) link member, plate, rod, etc. of this invention has been positioned thereover. Bolt portion 762 also include a bore 770 extending through hemispherically-shaped end 768, which bore aligns with bore 760 of screw portion 752 to receive means for fastening portions 752 and 762 together. The bore 770, however, includes a stepped portion 772 so that the enlarged head of a fastening means may be received in countersunk fashion so as to be substantially flush with the rounded portion of hemispherically-shaped end 768 of bolt portion 762. The end 768 of bolt portion 762 has serrations or other interdigitating structure 780 for locking same to the similarly configured face of end 758 of screw portion 752. The mating interdigitating surfaces may be in the form of serrations, ramped teeth, roughened surfaces or any other structure for rotationally locking the bolt portion 762 to the screw portion 752.

An example of one means for fastening the screw and bolt portions together is shown in FIG. 1A and includes a lag-type set screw 790 that is threaded so as to mate with the threaded bores 760, 770 of the respective screw and bolt portions. Alternative fastening means, e.g., a pin may be used instead of a set screw. The screw and bolt portions may be rotated with respect to each other and locked in position via set screw 790.

Referring to FIG. 1A, the hemispherically-shaped end portions 758, 768 of the respective screw and bolt portions 752, 762 are joined in face-to-face contact along the plane or equator 800 to form a substantially spherically-shaped central member 774 (with set screw 790 not in place). In a preferred embodiment of the multi-directional screw/bolt according to the present invention, the screw and bolt portions are coaxial, i.e., positioned so that the longitudinal axis of each extends along line 810, the pivot axis 820 about which the respective portions are rotatable forms an oblique angle with the aforementioned longitudinal axis 810. That is, when the screw and bolt portions are positioned so as to be coaxial, the longitudinal axis thereof does not form a right angle with the pivot axis about which the portions may rotate.

Another preferred embodiment of the invention is shown in FIG. 1B and includes a projection 763 on the face of bolt portion 762 and a mating recess 765 on the face of screw portion 752 (or vice-versa). The projection 763 and recess 765 serve to facilitate proper engagement of the components as well as provide the attachment member with added shear strength.

This aspect of the invention permits the bolt portion 762 to extend from the center of the sphere 774 formed by the joined screw and bolt hemispherically shaped ends, 758, 768. In other words, regardless of the angular position of bolt portion 762 relative to the screw portion 752, the threaded portion 764 of the bolt will always extend along a central axis of the aforementioned sphere. This feature permits the bolt 762 to engage the center of the opening in a plate, rod, etc. Since the bolt portion 762 of the invention extends outwardly from the sphere along a central axis thereof, the plate (or other element) opening can be received on the bolt with the latter centrally located therein, and with a concave depression properly seated on sphere 774. Locking nut 794 then is threaded over bolt extension 764 to securely fix the plate to the multi-directional attachment device 750. This provides an extremely stable and secure assembly.

Figure 1D:
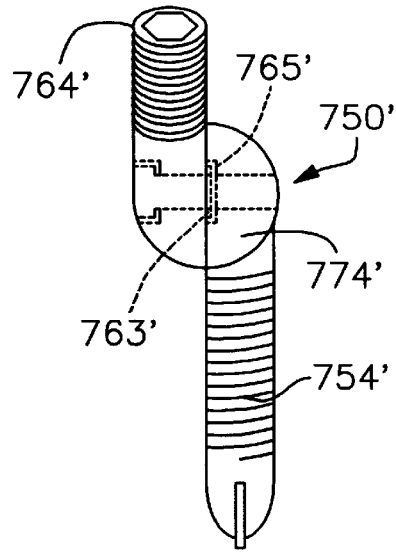

However, as seen in FIG. 1D, it also is possible to form a multi-directional attachment device 750' such that the bolt extension 764' does not extend from the center of the spherical portion 774' formed by the mating hemispherically-shaped end portions 768', 758'. The elongated screw section 754' also may not extend from the center of end spherical portion 774'. The embodiment shown in FIG. 1B, however, illustrates the preferred construction of the multi-directional attachment device of the present invention.

The benefits obtained by the ability to independently position the bolt portion 762 with respect to the screw portion 752 will be apparent to those skilled in the art. It is possible to position the screw portion in an optimal location in the vertebrae (or other bone) without concern as to the angle that the screw forms with the desired position of a plate, rod, etc., because the bolt portion can be adjusted relative to the screw portion so as to engage the plate in a perpendicular manner.

Figure 2A:
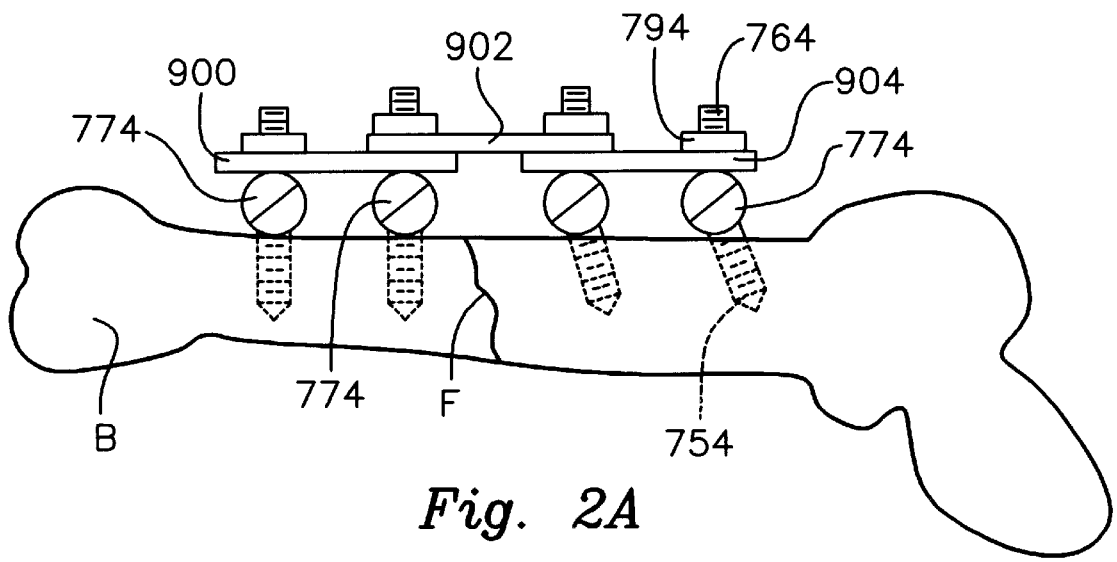
FIGS. 2A and 2B are identical to FIGS. 10A and 10B of application Ser. No. 08/692,821. As stated in that application.

In another aspect of the present invention, a bone fixation system is provided for external applications, such as stabilizing bones which have been fractured, e.g., long bones, pelvic bones, etc. FIG. 2A depicts an external bone fixation system secured to a long bone B having a fracture F therein. The system includes a plurality of plates 900, 902, 904 which may have a structure according to the form of the spinal implant plates discussed above with respect to the aforementioned embodiments. A plurality of multi-directional attachment members having spherical portions 774 are provided, these members preferably having a structure described above in connection with FIGS. 1A to 1C.

As can be seen in FIG. 2A, plate members 900 and 904 are secured to each portion of bone B on opposite sides of fracture F via respective pairs of multi-directional attachment members. These two plate members are joined to each other by a third plate member 902 the two ends of which respectively overlie an end of each plate 900, 904. The threaded section 754 of the screw portion 752 of each attachment member is positioned in an optimal location in bone B, and the extension 764 of the bolt portion 762 of each respective attachment member is angularly adjusted to engage the plate members in a desired fashion, e.g., perpendicularly. Locking nuts 794 are positioned on bolt portions 762 to lock the plates to the attachment members. This arrangement, which is a one-plane fixation of bone B, stabilizes the bone portions to permit healing of fracture F.

Figure 2B:
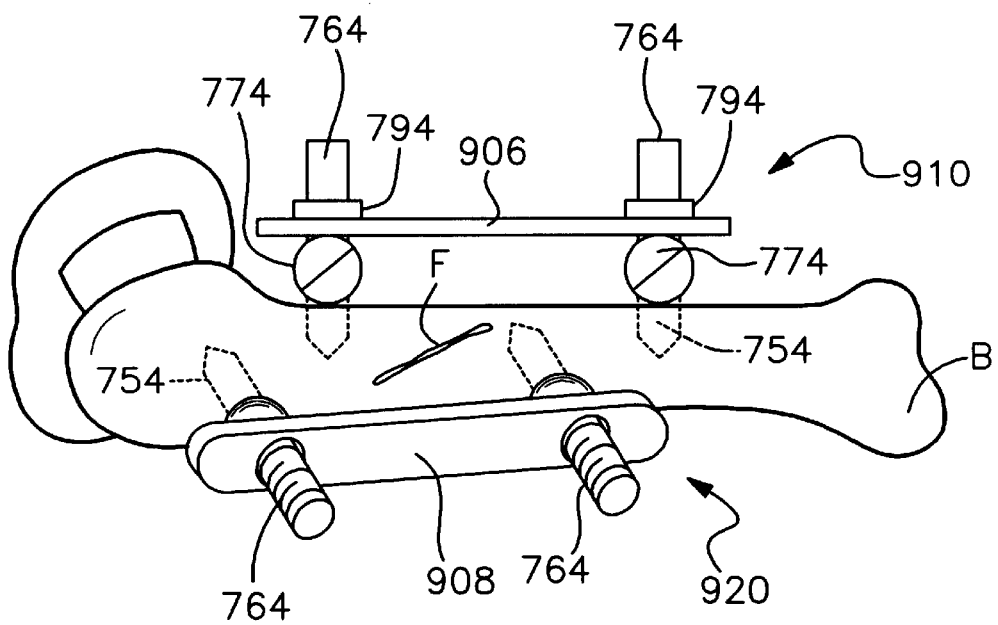

FIG. 2B depicts a two-plane fixation of a bone B with a fracture F. Specifically, a first fixation assembly 910 includes a plate member 906 secured to bone B in a first plane via a pair of multi-directional attachment members with spherical portions 774 formed by mating end portions of bolt and screw portions, and locking nuts 794 as described above. A second fixation assembly 920 includes a plate member 908 secured to bone B in a different plane via a second pair of attachment members (the locking washers not being attached to bolt extensions 764 on which plate 908 is mounted in FIG. 2B). The embodiment in FIG. 2B stabilizes the fractured bone B in two planes and is suitable, e.g., for use in applications requiring considerable stabilization forces.

Figure 3:
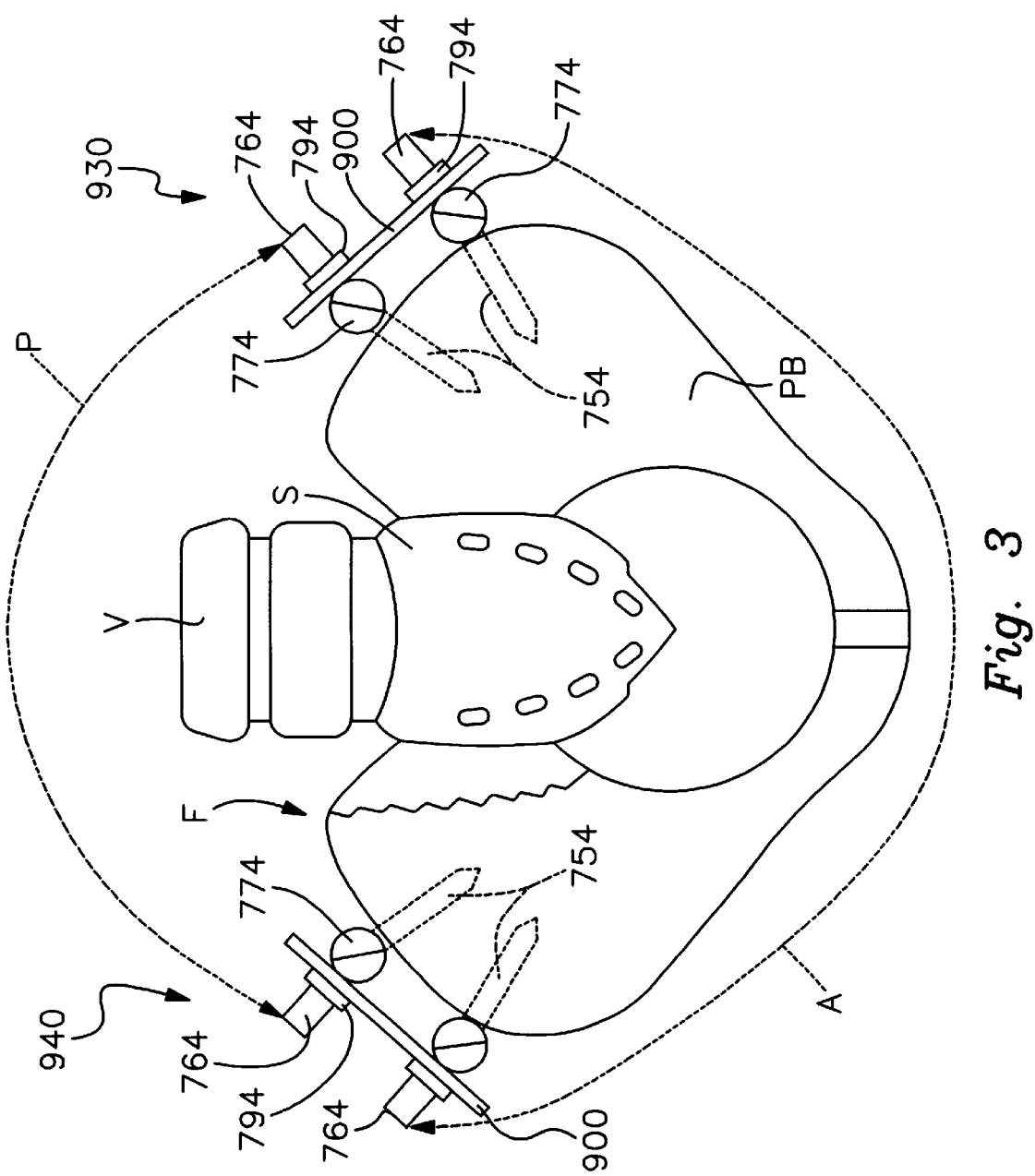
FIG. 3 is identical to FIG. 11 of application Ser. No. 08/692,821. As stated in that application.

FIG. 3 shows a further application of an external bone fixation system wherein the system is secured to a pelvic bone PB. The system includes a first fixation assembly 930 including a plate member 900 secured to a side of the pelvis via a pair of multi-directional attachment members having spherical portions 774. As seen in FIG. 3, the screw sections 754 are positioned at a desired location in the bone while the bolt extensions 764 are adjusted relative sections 754 to engage plate 900 in a perpendicular manner. A second fixation assembly 940 is secured to the opposite side of the pelvis via a second pair of attachment members. The respective fixation assemblies 930, 940 may be connected to each other by cross-link members (not shown) constructed according to the above-embodiments. Such connection of the plate assemblies may be carried out along the anterior (line A in phantom) or posterior (line P in phantom) surface of the pelvis.

Those skilled in the art will appreciate that the embodiments of FIGS. 2A, 2B and 3 illustrate only exemplary non-spinal applications of the bone-fixation systems according to the present invention. Other applications and uses, of course, will be apparent to persons skilled in the art.

Figure 4A:
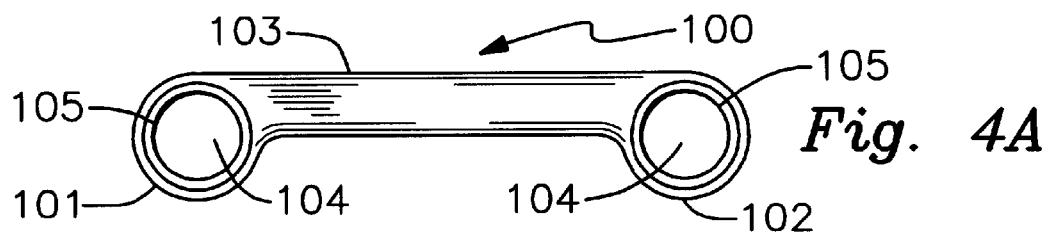
FIG. 4A is a top view of one form of a spinal implant link member of the invention.
Figure 4B:
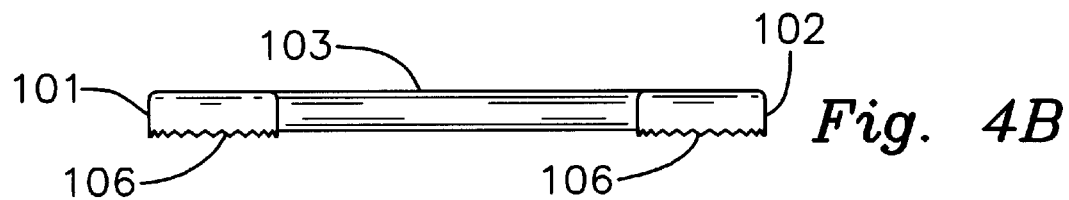
FIG. 4B is a front view of the spinal implant link member of FIG. 4A.
Figure 4C:
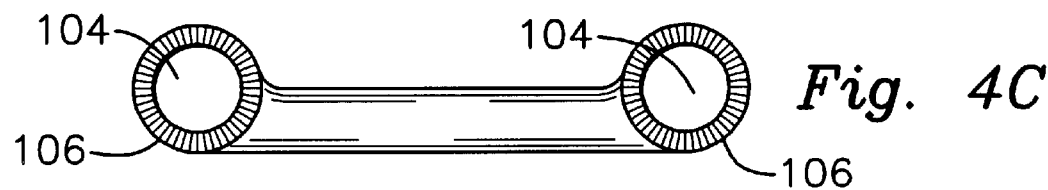
FIG. 4C is a bottom view of the spinal implant link member of FIG. 4A.

One form of novel link member useful in the system and method of this invention is shown by FIGS. 4A, 4B and 4C. As shown by the figures, the link 100 comprises opposite ends 101 and 102 connected by a central portion 103. Apertures 104 in the link ends are recessed at 105 to receive another spinal implant member which, for example, may be another link, a fixed or multi-directional screw, or a link tie means contoured to mate an aperture 105 in a link member. The aperture 105 may be contoured to mate with a shoulder or the like on another implant member such as a bone screw wherein an audible sound, e.g., a click, results when the link and the other implant member are properly mated.

As shown in FIGS. 4A to 4C, the link is flat. The invention also includes link members contoured to accommodate spinal curvature such as lordosis and kyphosis or to provide torsion in the link.

As shown by the figures, the central portion 103 of the link is generally rectangular in cross-section. The invention includes links of any desired cross-section.

FIG. 4B, a side view of the link, includes a digitated surface 106 adjacent the apertures 104 on one side of the link 100. The digital surface 106 may appear on only one or on both sides of the link 100, on one side at one end of the link, or on one side and one end of the link and on the other side at the other end of the link.

Figure 5A:
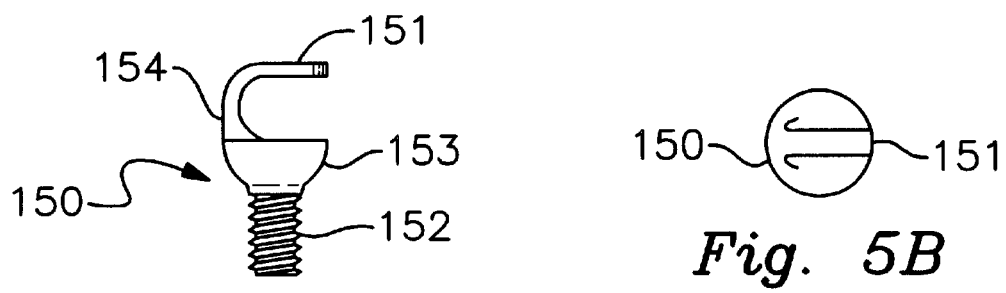
FIGS. 5A, 5B, 5C and 5D are side, front, top and bottom views of one form of a hook useful in the invention.
Figure 5B:
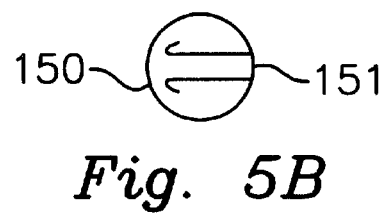
Figure 5C:
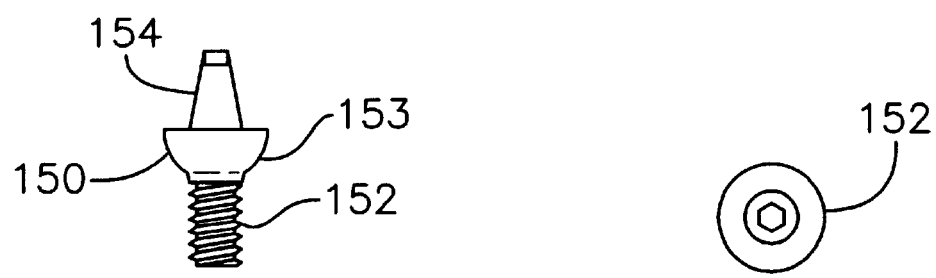
Figure 5D:
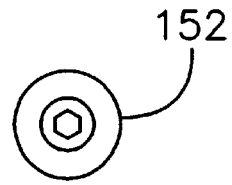
Figure 12:
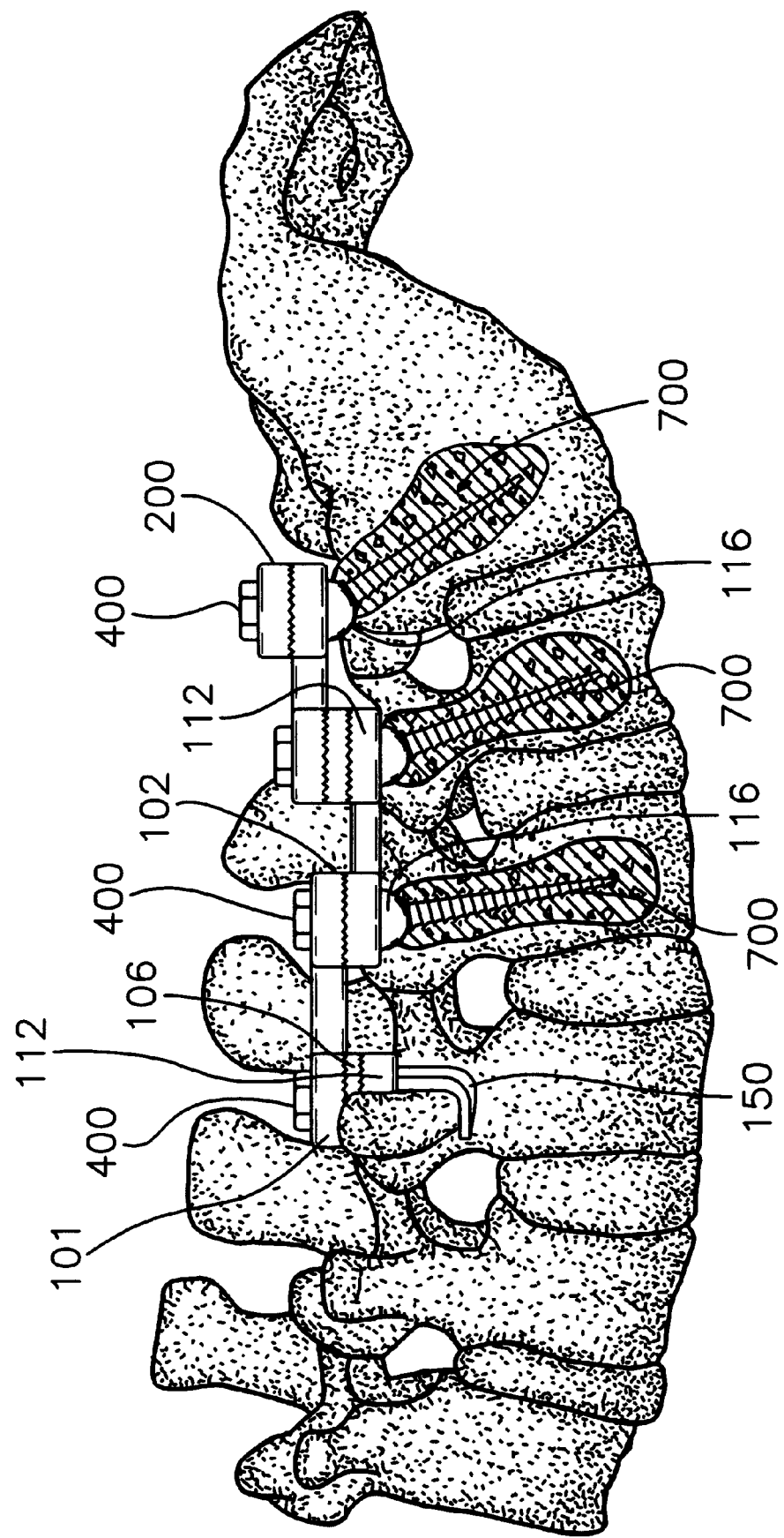
FIG. 12 is a side view of the FIG. 10 construct.

FIGS. 5A, B, C and D illustrate various views of one form of a hook 150 useful in the invention. As shown in the figures, the hook includes a hook element 151, and a threaded shaft 152 extending from a shouldered hemispherical base 153 from which the hook portion 154 extends. The hook 150 may be utilized in the implant system of the invention as illustrated by FIG. 12.

FIGS. 6A, 6B and 6C are exploded views showing one method for assembling various of the spinal implant members of the invention. FIG. 6A illustrates assembly of the member 300, a link 100, an apertured spacer 500, and threaded lock nut 200.

The tie member 300 includes a threaded shaft 302 extending upwardly from a base or step member 301. The shaft 302 has an open hexagonal top portion to accommodate a matching hexagonal head of a wrench.

The apertured end 101 of link 100 is positioned above the shaft 302 of the tie means 300 with the digitations 106 on top.

Link end-cap or spacer 500, positioned above the end 101 of the link 100 has a digitized lower perimeter 501 for engagement with the digital surface 106 of the apertured end 101 of the link 100.

Lock nut 200 has a rim portion 201, a downwardly extending internally threaded shaft portion 202, and a hexagonal aperture 203 to accommodate a hexagonal head of a wrench or other tightening or locking device. The elements are assembled as indicated by FIG. 6A. The threads 302 of the tie means 300 engage the internal threads of the lock nut 200. The digitations 501 of spacer 500 mesh with the digitations 106 of the link 100. The assembly is locked by use of a wrench means having a hexagonal head which passes through the hexagonal aperture 203 in the nut 200 through the assembly into the hexagonal aperture 303 in the tie means 300.

FIG. 6B includes in the assembly the apertured and digitized second end of the link 100, a second link 100A having apertured first and second ends 101A and 102A. The apertures are recessed at 105A and have digitations 106A at the bottom side of the link 100A.

In FIG. 6B the tie means includes an extension 304 which may be a helical portion of a fixed or multi-directional bone screw. The cap 200A is the same as the cap 200 of FIG. 6A. The elements of FIG. 6B are assembled in the order indicated by the figure in the manner described in FIG. 6A.

FIG. 6C incorporates a third link 100B as shown.

Figures 7, 8A, 8B:
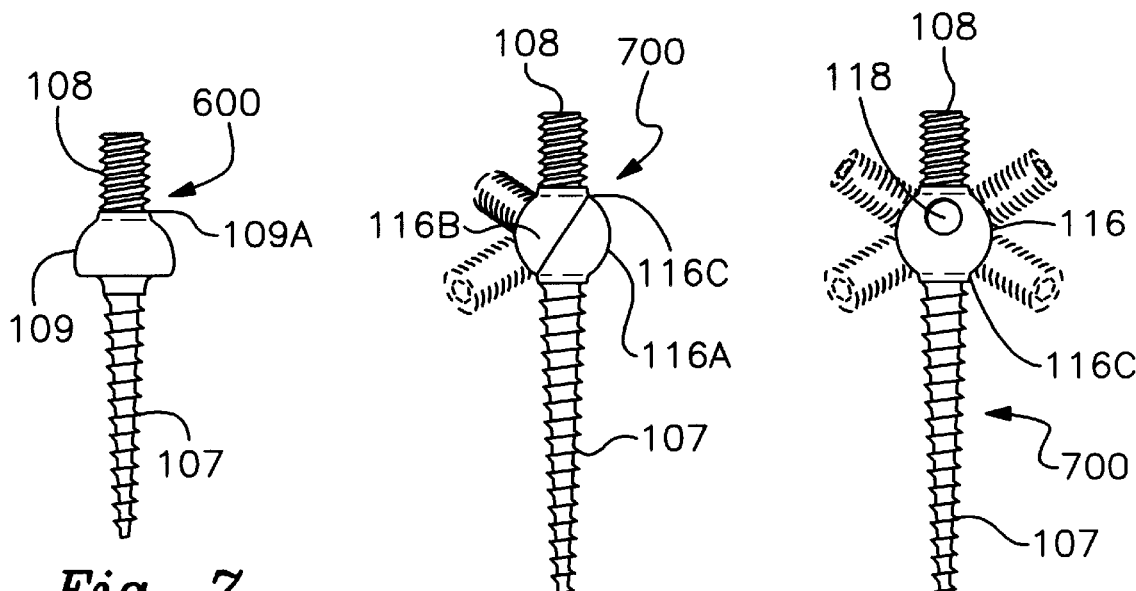
FIG. 7 is a side view of one form of a fixed bone screw.
FIG. 8A is a side view of another form of multi-directional bone screw.
FIG. 8B is a view of the FIG. 8B multi-directional bone screw.

FIG. 7 illustrates one view of a fixed bone screw 600 having a helical portion 107 for penetration, e.g., of a pedicle, a threaded shaft 117 extending upwardly from said helical portion. The helical portion 107 is connected to the shaft 108 by a hemispherically contoured portion 109 which has a shoulder 109A.

FIGS. 8A and 8B show a multi-directional screw 700 generally similar to the multi-directional screw 750 of FIGS. 1A, 1B and 1C. Like the fixed screw 600, the screw 750 has a helical portion 107 for penetration of a pedicle and a thread shaft 108 for insertion into and extension beyond a link aperture or apertures for attachment of a locking means such as a nut. The screw 700 includes a pin or screw means 118 for locking its hemispherical parts in a desired angular rotation instead of the screw used in the screw 750. The multi-directional screw shown in FIGS. 8A and 8B has a shoulder 116C for mating with a corresponding recess in a link or other implant member.

Figure 9:
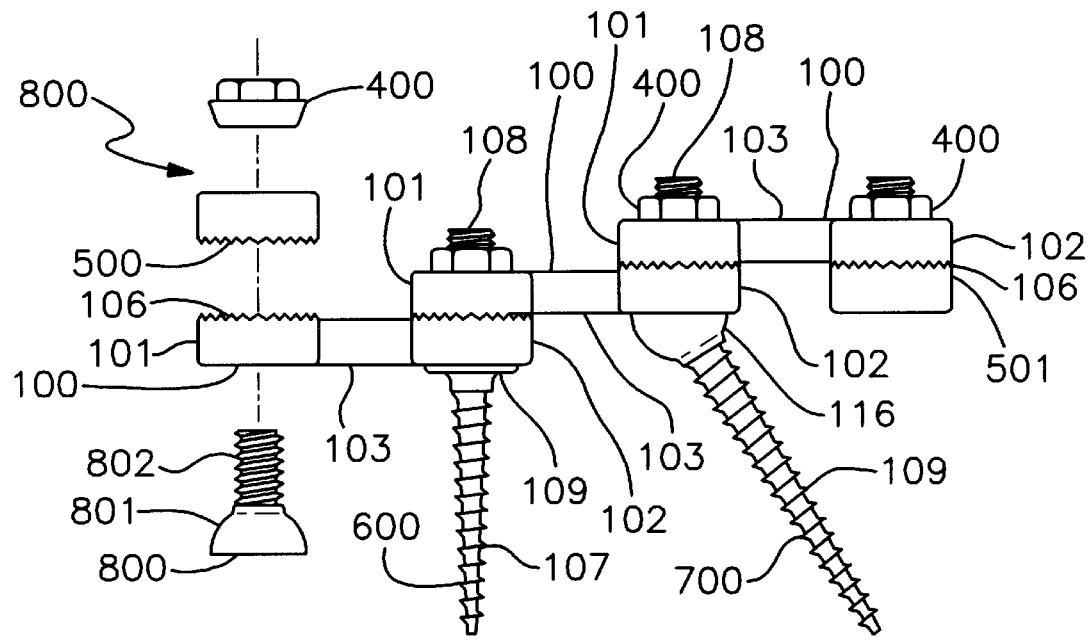
FIG. 9 illustrates one assembly of some of the spinal implant members of the invention. The assembly includes three links, a multi-directional screw, a fixed screw, a link tie and associated end caps.

FIG. 9 illustrates one assembly of implant elements of the invention. The FIG. 9 assembly includes bottom, middle and top interconnected links 100, a fixed screw 600, a multi-directional screw 700 and a link tie means 800 having a hemispherical base 801 and a threaded shaft 802 to extend through apertures of the bottom link 101 and a spacer 500 to be secured by the nut 400.

The bottom surface of the link apertures are concave hemispherically contoured to mate with the correspondingly convex and in preferred embodiments, shouldered hemispherical or spherical portions of the tie means and the fixed and multi-directional screws.

Figure 10:
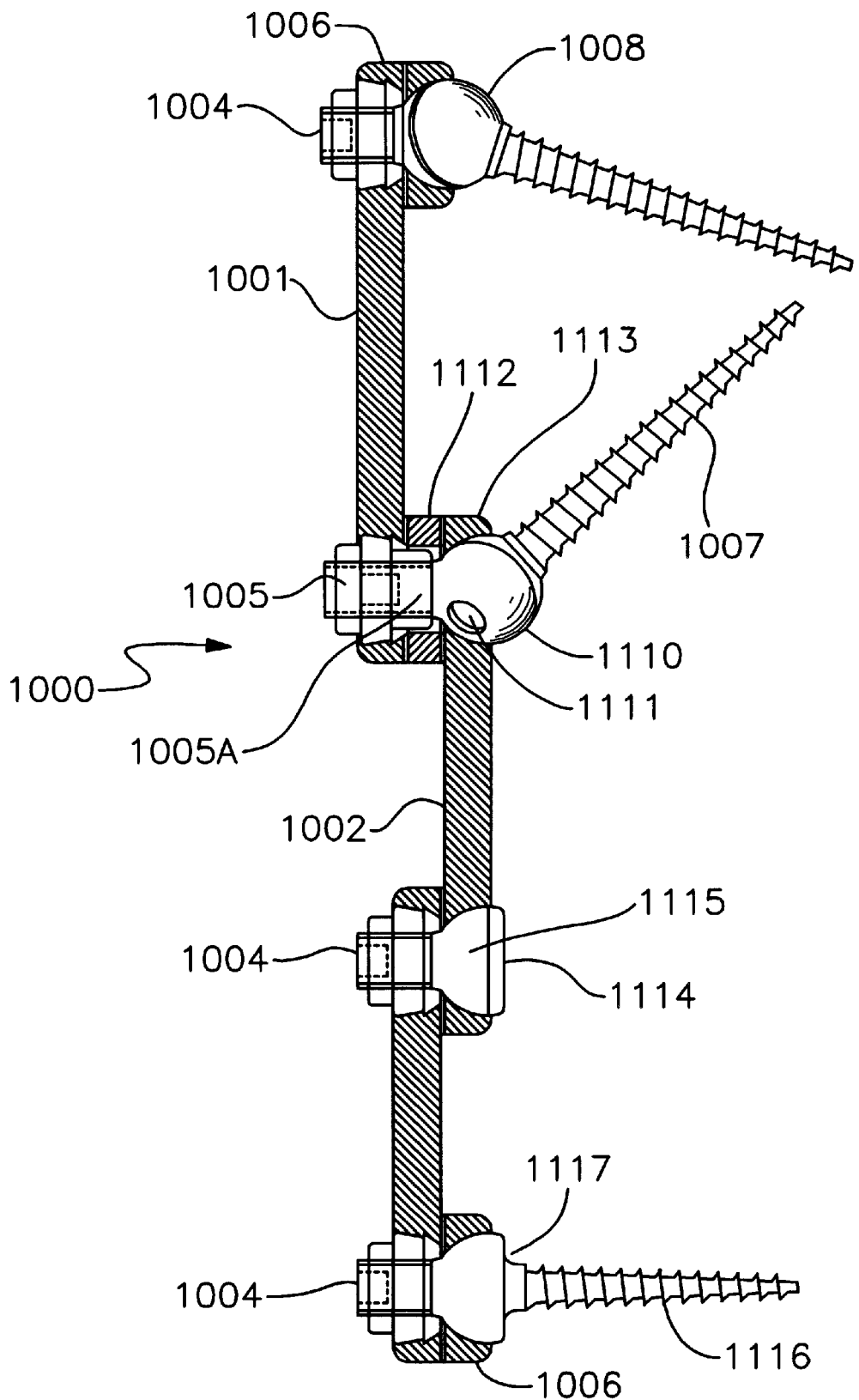
FIG. 10 shows another assembly of spinal implant members of the invention. The FIG. 10 assembly includes two top links, a bottom link, two polydirectional screws, three implant member end caps 1005, one extended implant member end cap 1005A, end cap securing means 1004, a spacer 112 positioned between two of the links and two contoured washers to accommodate attachment of an implant member, e.g., a fixed or polydirectional screw to a link.

FIG. 10 illustrates a second assembly 1000 of various spinal implant members of the invention. Assembly 1000 comprises a first top link 1001, a middle bottom link 1002 and a second top link 1003.

The assembly includes washers 1006 positioned below a terminal aperture of the links 1001 and 1003. The washers 1006 are internally contoured to mate with a generally hemispherical or shouldered contour of the midportion of fixed screw 1116 and the multi-directional screw 1008.

The apertured ends of the middle link are contoured to receive the shouldered hemispherical surface 1115 of the base of the link tie means 1114 and of the midportion of the polydirectional screw 1007.

Figure 11:
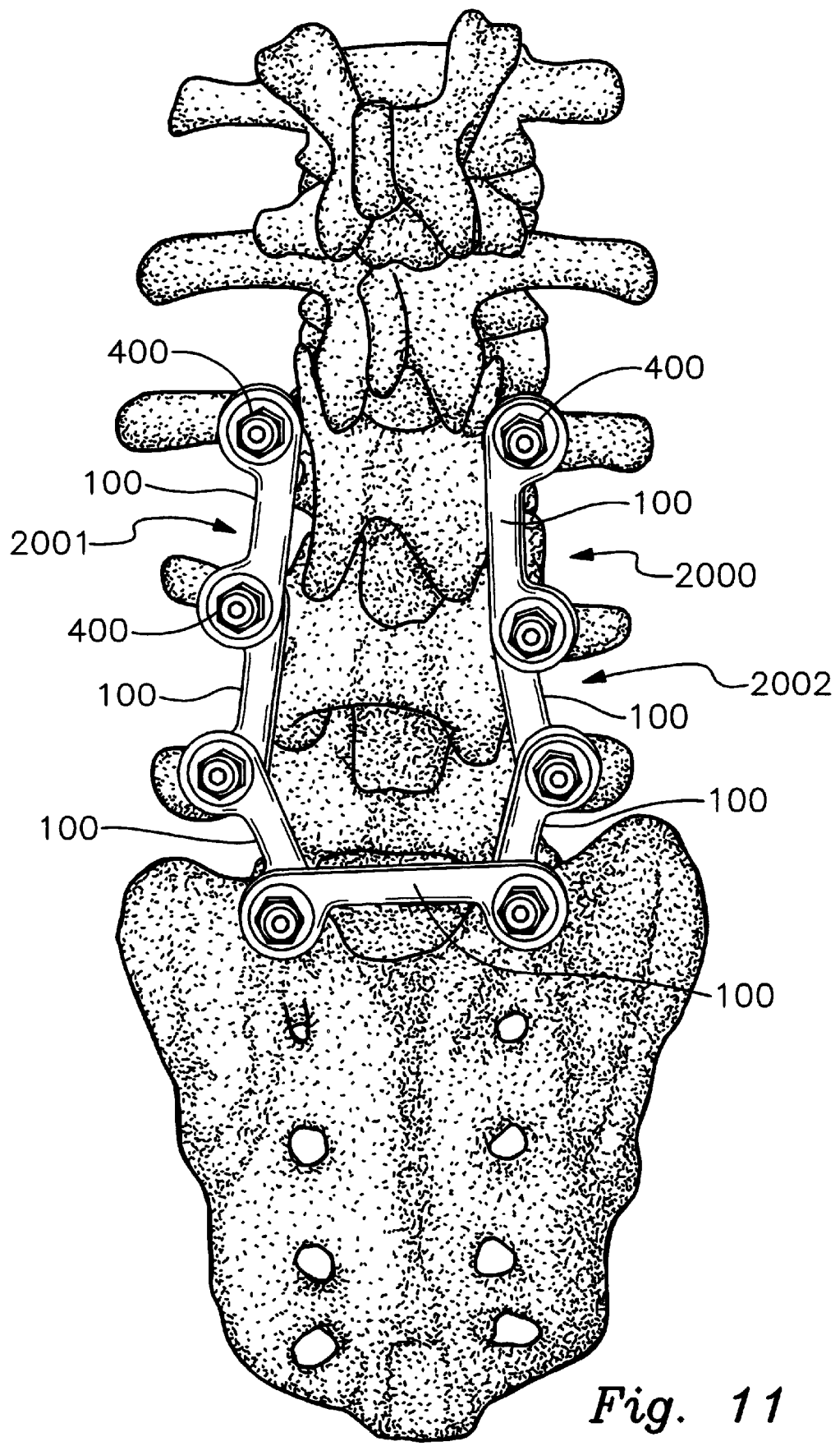
FIG. 11 is a front view of a multilevel spinal implant construct of the invention. The construct as shown includes two three link contra-lateral chains connected directly to a transverse link.

FIG. 11 is a front view of a three level construct 2000 formed from links, screws, lock nuts and related spinal implant elements which the invention may include.

As shown in FIG. 11 the construct 2000 comprises two lateral columns 2001 and 2002 each comprising a chain of three links 100. The columns 2001 and 2002 are connected at the distal ends by single, transverse link 100. Alternatively, the single transverse link may be replaced by a transverse element comprising two or more links 100 connected by a bone screw.

The construct is fixed to the spine by a plurality of fixed and multi-directional screws and associated end caps 400.

The fixation of the construct to the spine is best shown by the FIG. 12 vertical section of FIG. 11. Referring to FIG. 12, the construct comprises three multi-directional screws 109 and one hook member 150.

Figure 13:
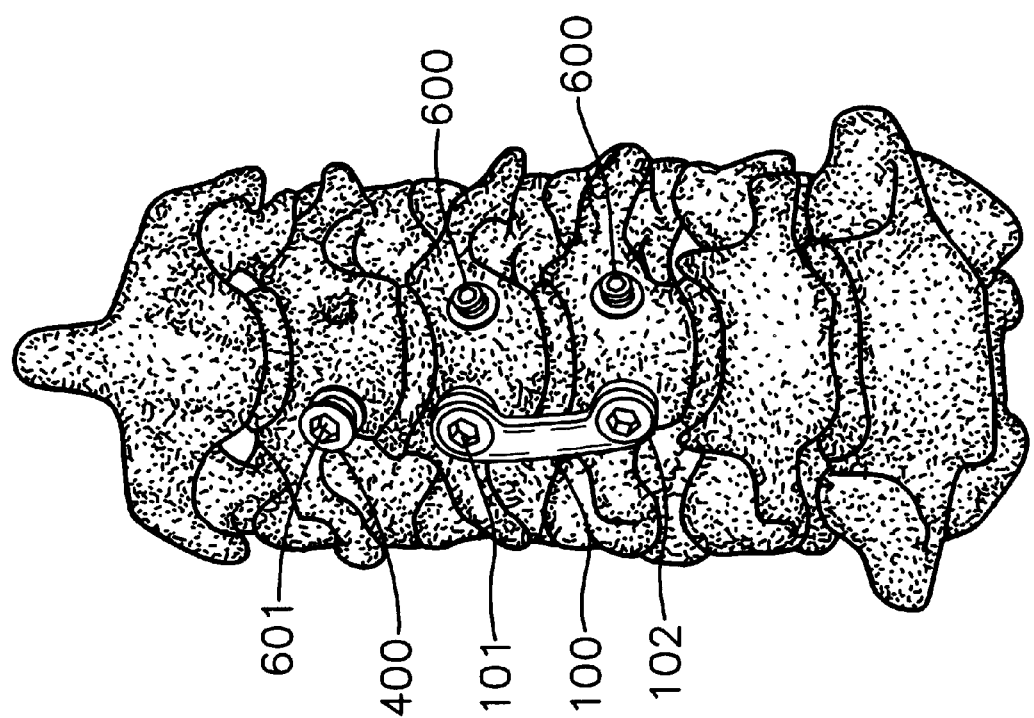
FIG. 13 illustrates a one level anterior construct.

FIG. 13 illustrates a one level construct including a single link 100 and associated fastening means, including fixed or multi-directional screws and lock nuts or end caps. FIG. 13 includes two screws 600 inserted in a vertebrae on which a second link 100 may be positioned and one inserted screw 601 having an end cap 400.

Figure 14:
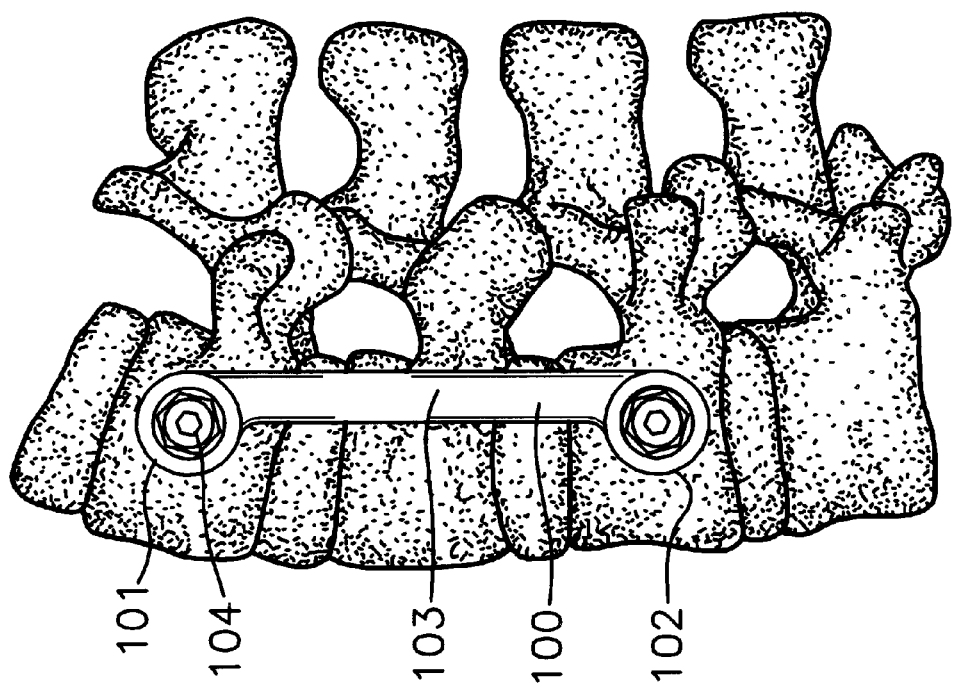
FIG. 14 illustrates an anterior construct including an appropriately dimensioned link.

FIG. 14 illustrates an anterior construct including a suitably dimensioned link secured to a spine by screws and end caps or locking nuts.

I claim:

1. A flat spinal implant link member comprising
   (i) a first end adapted to be affixed to a vertebra;
   (ii) a second end adapted to be affixed to a second vertebra;
   (iii) a central portion connecting said first end and said second end:
   (iv) an aperture having a middle portion in said first end and in said second end;
      wherein said central portion (iii) is offset from a line extended between middle portions of each of said apertures in said first and second ends of said implant member; and
   (v) means for engaging at least one of said first end (i) or said second end (ii) of said implant member with a first or second end of another implant member when at least one of said apertures of each of said implant members are superimposed.

2. The claim 1 spinal implant member where said means for engaging (v) further comprises means for locking said another claim 1 member at any desired angle relative to the claim 1 spinal implant member with which it is engaged.

3. The claim 1 spinal implant member wherein said means for engaging (v) comprises a digitated surface adjacent at least one side of at least one of said apertures of said first end (i) or second end (ii) of said claim 1 implant member.

4. The claim 3 spinal implant member wherein said digitated surface comprises radial serrations around at least a portion of said at least one aperture.

5. The claim 1 spinal implant member wherein said means for engaging (v) comprises a digitated surface adjacent said aperture of said at least first end (i) or said second end (ii) of said claim 1 link member and wherein said first or second end of said another link member has a digitated surface matching said digitated surface of said claim 1 link member.

6. The claim 1 implant link member wherein said means for engaging element (v) is a digitated surface and wherein said digitated surface
   (i) is adjacent only one of said apertures; or
   (ii) is adjacent both of said apertures; or
   (iii) is present on one side only of only one of said apertures of said member; or
   (iv) is present on both sides of one or both of said apertures of said member.

7. A flat spinal implant link member comprising
   (i) a first end adapted to be affixed to a vertebra;
   (ii) a second end adapted to be affixed to a second vertebra;
   (iii) a central portion connecting said first end and said second end;
   (iv) an aperture having a middle portion in said first end and in said second end;
      wherein said central portion (iii) is offset from a line extended between middle portions of each of said apertures in said first and second ends of said implant member; and
   (vi) tie means engaging at least one of said first end (i) or said second end (ii) of said implant member with a first or second end of another implant member
      wherein said tie means comprises a base portion and a shaft which extends upwardly from said base portion through and beyond superimposed apertures of said first or second end portions of said first and said another spinal implant members.

8. The spinal implant member of claim 7 further comprising
   (vii) securing means engaging said portion of said shaft which extends beyond said apertures of said first and said another claim 7 implant members.

9. A flat spinal implant link member comprising
   (i) a first end adapted to be affixed to a vertebra;
   (ii) a second end adapted to be affixed to a second vertebra;
   (iii) a central portion connecting said first end and said second end;
   (iv) an aperture having a middle portion in said first end and in said second end;
      wherein said central portion (iii) is offset from a line extended between middle portions of each of said apertures in said first and second ends of said implant member; and
      wherein at least one of said apertures in said first and second ends is recessed and wherein said recess is shaped to receive a matching shaped surface of another spinal implant member.

10. The claim 9 spinal implant member wherein said recess in said at least one of said apertures is hemispherical.

11. The claim 10 spinal implant member wherein said another spinal implant element is
    a means tying a claim 1 spinal implant member to another spinal implant member; or
    a fixed screw; or
    a multi-directional screw; or
    a hook.

12. A spinal implant assembly comprising
    (i) a top link member wherein said top length member comprises an apertured first end, and apertured second end and a central portion connecting said first and second ends; and
    (ii) a bottom link member comprising an apertured first end, an apertured second end, and a central portion connecting said first and second ends,
       wherein said apertures in at least one of said ends of said top or bottom link members are superimposed;
    (iii) another spinal implant member comprising a shaft extending through and beyond said superimposed apertures wherein said another spinal implant member is a multi-directional screw and wherein said multi-directional screw comprises a bone screw portion and a bolt portion;
    (iv) means for securing said shaft in said superimposed apertures of said top and bottom link members; and
    (v) an apertured spacer between said superimposed apertures of said top and bottom link members, wherein said shaft of said another spinal implant member extends through and beyond the superimposed apertures of said top and bottom link members and the aperture of said spacer.

13. The claim 12 spinal implant assembly wherein said another spinal implant member (iii) comprises
    (i) a means for engaging at least two spinal implant link members; or
    (ii) a fixed screw; or
    (iii) a multi-directional screw; or
    (iv) a hook.

14. The claim 12 spinal implant assembly wherein said shaft of said another spinal implant member is threaded and wherein said means (iv) for securing said shaft is a nut engaging said threaded shaft.

15. The claim 12 spinal implant assembly wherein said means (iv) for securing said shaft further comprises means for locking said top and bottom implant link members in any desired angular relationship.

16. The claim 12 spinal implant assembly wherein at least one of said apertures of top or said bottom link members comprises a contoured recess to receive a matching contoured surface of said another spinal implant member.

17. The claim 12 spinal implant assembly wherein at least one of said apertures of top or said bottom link members comprises a contoured, tapered recess to receive a matching contoured and tapered surface of said another spinal implant member.

18. The claim 12 spinal implant assembly wherein
   (i) at least one of said link end apertures of said top link or said bottom link is recessed and wherein said recess is contoured to receive a mating contoured surface on said another spinal implant member.

19. The claim 18 spinal implant assembly wherein said at least one of said link end apertures is a generally hemispherical recess.

20. A spinal implant assembly comprising:
   (i) a top link member wherein said top length member comprises an apertured first end, and apertured second end and a central portion connecting said first and second ends; and
   (ii) a bottom link member comprising an apertured first end, an apertured second end, and a central portion connecting said first and second ends,
      wherein said apertures in at least one of said ends of said top or bottom link members are superimposed;
   (iii) another spinal implant member comprising a shaft extending through and beyond said superimposed apertures wherein said another spinal implant member is a multi-directional screw and wherein said multi-directional screw comprises a bone screw portion and a bolt portion;
   (iv) means for securing said shaft in said superimposed apertures of said top and bottom link members; and
   (v) apertured washer means positioned below at least one of said link end apertures;
      wherein the distal side of said washer means is contoured to receive a correspondingly contoured mating surface of said another spinal implant member.

21. The claim 20 spinal implant assembly in which said apertured washer means is contoured to receive a generally hemispherical mating surface of said another spinal implant member.

22. The claim 21 spinal implant assembly wherein said another spinal implant member comprises
   (i) a means for engaging at least two spinal implant link members; or
   (ii) a fixed screw; or
   (iii) a multi-directional screw; or
   (iv) a hook.

23. A spinal implant assembly comprising
   (i) a top spinal implant link member wherein said top link member comprises an apertured first end, an apertured second end and a central portion connecting said first and second ends;
   (ii) a spinal implant screw having a helical portion, a shaft portion extending upwardly from said helical portion and a contoured surface between said helical portion and said shaft portion; and
      wherein said shaft portion of said screw extends upwardly through at least one of said apertured ends of said implant link member; and
   (iii) washer means positioned between said contoured surface of said spinal implant screw and said spinal implant link wherein the distal side of said washer means is contoured to mate with said contoured surface of said screw, and wherein said washer means extends beyond said implant link member such that the combination of said washer means and said implant link member is greater in thickness than the thickness of either said washer means or said implant link member alone.
   (iv) a bottom spinal implant member wherein said bottom link member comprises apertured first and second ends and wherein one of said first end or said second end of said bottom link member is engaged with a first or second end of said top spinal implant link member, so that apertures of each of said implant members are superimposed.

24. The claim 23 spinal implant assembly wherein said contoured surface of said screw is generally hemispherical.

25. The claim 23 spinal implant assembly wherein said spinal implant screw is a multi-directional screw.

26. The claim 23 spinal implant assembly wherein said spinal implant screw is a fixed screw.

27. The claim 23 spinal implant assembly wherein said spinal implant screw is self-tapping.

* * * * *